(12) United States Patent
Morgan et al.

(10) Patent No.: US 6,194,188 B1
(45) Date of Patent: Feb. 27, 2001

(54) **TYPE II RESTRICTION ENDONUCLEASE, HPYCH4IV, OBTAINABLE FROM *HELICOBACTER PYLORI* CH4 AND A PROCESS FOR PRODUCING THE SAME**

(75) Inventors: Richard D. Morgan, Middleton, MA (US); Qing Xu, Nashville, TN (US)

(73) Assignees: New England Biolabs, Inc., Beverly, MA (US); Vanderbilt University, Nashville, TN (US)

( * ) Notice: Subject to any disclaimer, the term of this patent is extended or adjusted under 35 U.S.C. 154(b) by 0 days.

(21) Appl. No.: 09/404,671

(22) Filed: Sep. 23, 1999

(51) Int. Cl.$^7$ .............................. C12N 9/22; C12P 21/04; C07K 1/00
(52) U.S. Cl. ................... 435/199; 435/71.1; 530/350; 530/825
(58) Field of Search ................... 530/820, 825, 530/806, 350, 300; 536/23.2, 23.7; 424/94.1, 234.1; 935/11, 14; 435/199, 71.1

(56) References Cited

U.S. PATENT DOCUMENTS 5,200,333   4/1993  Wilson .............................. 435/172.3
6,133,009 * 10/2000 Morgan et al. ...................... 435/199

OTHER PUBLICATIONS

Robert et al. Nucleic Acid Res. 27: 312–313, Jan. 1999.*
Baik et al. In: Abstracts of the ASM 98th General Meeting, Atlanta, Georgia, May 17–21, 1998, vol. 98, pp. 20, abstract B–386, 1990.*
Endow, et al., J. Mol. Biol. 112:521 (1977).
Waalwijk, et al., Nucleic Acids Res., 5:3231 (1978).
Gingeras, et al., Proc. Natl. Acad. Sci., 80:402 (1983).
Gingeras, et al., Nucleic Acids Res. 5:4105 (1978).
Sanger, et al., Proc. Natl. Acad. Sci., 74:5463 (1977).
Brown, et al., J. Mol. Biol. 140:143 (1980).
Deverenx, et al., Nucleic Acids Res. 12:387 (1984).
Atlschul, et al., J. Mol. Biol. 215:403 (1990).
Gish, et al., Nature Genet., Mar. 20, 2000 3:266 (1993).

* cited by examiner

Primary Examiner—Lynette R. F. Smith
Assistant Examiner—S. Devi
(74) Attorney, Agent, or Firm—Gregory D. Williams (57) ABSTRACT

In accordance with the present invention, there is provided a novel restriction endonuclease and its DNA obtainable from *Helicobacter pylori* CH4 (NEB#1236), hereinafter referred to as "HpyCH4IV", which endonuclease:

(1) recognizes the nucleotide sequence 5'-ACGT-3' to in a double-stranded DNA molecule as shown below,
5'-A↓CGT-3'
3'-TGC↑A-5'
(wherein G represents guanine, C represents cytosine, A represents adenine, T represents thymine and N represents either G, C, A, or T);

(2) cleaves said sequence in the phosphodiester bonds between the A and C as indicated with the arrows; and (3) cleaves double-stranded PhiX174 DNA to produce 19 fragments, including fragments of 1036, 749, 397, 379, 371, 365, 362, 343, 282, 282, 268 base pairs, and 8 fragments smaller than 200 base pairs.

3 Claims, 5 Drawing Sheets

```
                10                  30                  50
      CGGAACTTTAAAAGATTAAGAAATAGTCTTAACCCAATCTCAAAAAAGAACTTTAAGTTT
  1   ---------+---------+---------+---------+---------+---------+  60

70                  90                 110
      TTACTCCATTTAAAAAGTGTGGGTTTAGATGAAAGGAAAAAATAAAACTTGTATAAGGTA
 61   ---------+---------+---------+---------+---------+---------+ 120
                                                       L  Y  K  V 130                 150                 170
      GCAGATATTTTTTGTGGCGCTGGAGGATTGAGTTATGGCTTTTCTATGCACCCTTATTTT
121   ---------+---------+---------+---------+---------+---------+ 180
       A  D  I  F  C  G  A  G  G  L  S  Y  G  F  S  M  H  P  Y  F 190                 210                 230
      GAATTAATATGGGCTAACGATATAGACAAGGATGCCATTTTAAGCTATCAAGCCAATCAT
181   ---------+---------+---------+---------+---------+---------+ 240
       E  L  I  W  A  N  D  I  D  K  D  A  I  L  S  Y  Q  A  N  H 250                 270                 290
      AAAGAAACGCAAACCATTTTATGCGATATTATGCAACTTAATTGCCACAACTTACCATGC
241   ---------+---------+---------+---------+---------+---------+ 300
       K  E  T  Q  T  I  L  C  D  I  M  Q  L  N  C  H  N  L  P  C 310                 330                 350
      GTTTCAATTGATATTCTACTAGGCGGACCACCATGCCAGAGCTATTCTACCCTTGGCAAA
301   ---------+---------+---------+---------+---------+---------+ 360
       V  S  I  D  I  L  L  G  G  P  P  C  Q  S  Y  S  T  L  G  K 370                 390                 410
      AGAAAAAATGGATGAAAAAGCGAATCTGTTTAAAGAATATTTGCGGCTCTTAGATTTAGTA
361   ---------+---------+---------+---------+---------+---------+ 420
       R  K  M  D  E  K  A  N  L  F  K  E  Y  L  R  L  L  D  L  V 430                 450                 470
      AAACCAAAAATGTTTGTCTTTGAAAATGTGGTGGGTTTAATGTCTATGCAAAAAGGGCAA
421   ---------+---------+---------+---------+---------+---------+ 480
       K  P  K  M  F  V  F  E  N  V  V  G  L  M  S  M  Q  K  G  Q 490                 510                 530
      TTATTCAAACAAATTTGTAACGCTTTTAAAGAGAGAGGTTATATCTTAGAGCATGCCATT
481   ---------+---------+---------+---------+---------+---------+ 540
       L  F  K  Q  I  C  N  A  F  K  E  R  G  Y  I  L  E  H  A  I 550                 570
      TTAAACGCCCTAGATTATGGTGTCCCTCAAATAAGGGAGCGAGTG
541   ---------+---------+---------+---------+----- 585
       L  N  A  L  D  Y  G  V  P  Q  I  R  E  R  V
```

FIG. 3B

```
              10                  30                  50
     ATGTGGTGGGAAAAACCAGCCCCCACTATTACAAGAAATTTTTCTACCCCAAGCAGTTCT
  1  ---------+---------+---------+---------+---------+---------+  60
      M  W  W  E  K  P  A  P  T  I  T  R  N  F  S  T  P  S  S  S 70                  90                 110
     AGGTGTATCCATCCAAGAGACTCTAGAGCGTTAAGCATTAGAGAGGGGGCAAGATTGCAA
 61  ---------+---------+---------+---------+---------+---------+ 120
      R  C  I  H  P  R  D  S  R  A  L  S  I  R  E  G  A  R  L  Q 130                 150                 170
     AGCTTTCCTGATAATTATAAATTCTGTGGGAGCTCTAGCGCTAAAAGATTGCAAATTGGC
121  ---------+---------+---------+---------+---------+---------+ 180
      S  F  P  D  N  Y  K  F  C  G  S  S  S  A  K  R  L  Q  I  G 190                 210                 230
     AATGCCGTGCCGCCTTTATTGAGTGTAGCGCTCGCTCATGCTGTCTTTGATTTTTTAAGG
181  ---------+---------+---------+---------+---------+---------+ 240
      N  A  V  P  P  L  L  S  V  A  L  A  H  A  V  F  D  F  L  R 250                 270                 290
     GGTAAAAATGTTTGATAATAACGATTTTAAAGGTTATAGAAATTTATTGGGTTTTAATTC
241  ---------+---------+---------+---------+---------+---------+ 300
      G  K  N  V  *  *  *

310                 330                 350
     TCAAAATGCGTTTAAGGAATTTTTAGGCGCTAAAGACATACAGCCTTGCGTTGATTTCAA
301  ---------+---------+---------+---------+---------+---------+ 360

370                 390                 410
     TTATTTAAACGCGCTCAAAAAAAGGCTTATTGAAATTTTTAGCGCTATCAATAGTGTTTA
361  ---------+---------+---------+---------+---------+---------+ 420

430                 450                 470
     TTGTTTTAAATATAATGAGTATGAATTGGAATGCTTTTTTAAAAACTCCATAGAGCGAGT
421  ---------+---------+---------+---------+---------+---------+ 480

490                 510                 530
     GTTTTCAAAGATAGTGGATACTCATATTATTTATAAGCTGAATAATCAAGGCAGAAGACC
481  ---------+---------+---------+---------+---------+---------+ 540

550                 570
     TGAAGAAGTGTGTTTTCTTGGATGCGTGGGTTTTTAGTAGCG
541  ---------+---------+---------+---          583
```

FIG. 3C

```
              10                  30                  50
    ATGTGGTGGGAAAAACCAGCCCCCACTATTACAAGAAATTTTTCTACCCCAAGCAGTTCT
  1 ---------+---------+---------+---------+---------+---------+  60

70                  90                 110
    AGGTGTATCCATCCAAGAGACTCTAGAGCGTTAAGCATTAGAGAGGGGGCAAGATTGCAA
 61 ---------+---------+---------+---------+---------+---------+ 120

130                 150                 170
    AGCTTTCCTGATAATTATAAATTCTGTGGGAGCTCTAGCGCTAAAAGATTGCAAATTGGC
121 ---------+---------+---------+---------+---------+---------+ 180

190                 210                 230
    AATGCCGTGCCGCCTTTATTGAGTGTAGCGCTCGCTCATGCTGTCTTTGATTTTTTAAGG
181 ---------+---------+---------+---------+---------+---------+ 240

250                 270                 290
    GGTAAAAATGTTTGATAATAACGATTTTAAAGGTTATAGAAATTTATTGGGTTTTAATTC
241 ---------+---------+---------+---------+---------+---------+ 300
              M  F  D  N  N  D  F  K  G  Y  R  N  L  L  G  F  N  S 310                 330                 350
    TCAAAATGCGTTTAAGGAATTTTTAGGCGCTAAAGACATACAGCCTTGCGTTGATTTCAA
301 ---------+---------+---------+---------+---------+---------+ 360
     Q  N  A  F  K  E  F  L  G  A  K  D  I  Q  P  C  V  D  F  N 370                 390                 410
    TTATTTAAACGCGCTCAAAAAAAGGCTTATTGAAATTTTTAGCGCTATCAATAGTGTTTA
361 ---------+---------+---------+---------+---------+---------+ 420
     Y  L  N  A  L  K  K  R  L  I  E  I  F  S  A  I  N  S  V  Y 430                 450                 470
    TTGTTTTAAATATAATGAGTATGAATTGGAATGCTTTTTTAAAAACTCCATAGAGCGAGT
421 ---------+---------+---------+---------+---------+---------+ 480
     C  F  K  Y  N  E  Y  E  L  E  C  F  F  K  N  S  I  E  R  V 490                 510                 530
    GTTTTCAAAGATAGTGGATACTCATATTATTTATAAGCTGAATAATCAAGGCAGAAGACC
481 ---------+---------+---------+---------+---------+---------+ 540
     F  S  K  I  V  D  T  H  I  I  Y  K  L  N  N  Q  G  R  R  P 550                 570
    TGAAGAAGTGTGTTTTTCTTGGATGCGTGGGTTTTTAGTAGCG
541 ---------+---------+---------+---------+--- 583
      E  E  V  C  F  S  W  M  R  G  F  L  V  A
```

TYPE II RESTRICTION ENDONUCLEASE, HPYCH4IV, OBTAINABLE FROM *HELICOBACTER PYLORI* CH4 AND A PROCESS FOR PRODUCING THE SAME

BACKGROUND OF THE INVENTION

The present invention relates to a new Type II restriction endonuclease, HpyCH4IV, obtainable from *Helicobacter pylori* CH4, and to the process for producing the same.

Restriction endonucleases are a class of enzymes that occur naturally in bacteria. When they are purified away from other contaminating bacterial components, restriction endonucleases can be used in the laboratory to break DNA molecules into precise fragments. This property enables DNA molecules to be uniquely identified and to be fractionated into their constituent genes. Restriction endonucleases have proven to be indispensable tools in modern genetic research. They are the biochemical 'scissors' by means of which genetic engineering and analysis is performed.

Restriction endonucleases act by recognizing and binding to particular sequences of nucleotides (the 'recognition sequence') along the DNA molecule. Once bound, they cleave the molecule within, or to one side of, the sequence. Different restriction endonucleases have affinity for different recognition sequences. The majority of restriction endonucleases recognize sequences of 4 to 6 nucleotides in length, although recently a small number of restriction endonucleases which recognize 7 or 8 uniquely specified nucleotides have been isolated. Most recognition sequences contain a dyad axis of symmetry and in most cases all the nucleotides are uniquely specified. However, some restriciton endonucleases have degenerate or relaxed specificities in that they recognize multiple bases at one or more positions in their recognition sequence, and some restriction endonucleases recognize asymmetric sequences. HaeIII, which recognizes the sequence 5'-GGCC-3', is an example of a restriction endonuclease having a symmetrical, non-degenerate recognition sequence, while HaeII, which recognizes 5'-(Pu)GCGC(Py)-3' typifies restriction endonucleases having a degenerate or relaxed recognition sequence. Endonucleases with symmetrical recognition sequences generally cleave symmetrically within or adjacent to the recognition site, while those that recognize asymmetric sequences tend to cleave at a distance of from 1 to 18 nucleotides away from the recognition site. More than two hundred unique restriction endonucleases have been identified among several thousands of bacterial species that have been examined to date.

Endonucleases are named according to the bacteria from which they are derived. Thus, the species *Haemophilus aegyptius*, for example synthesizes 3 different restriction endonucleases, named HaeI, HaeII and HaeIII. These enzymes recognize and cleave the sequences 5'-(W)GGCC(W)-3' (SEQ ID NO:1), 5'-(Pu)GCGC(Py)-3' and 5'-GGCC-3' respectively. *Escherichia coli* RY13, on the other hand, synthesizes only one enzyme, EcoRI, which recognizes the sequence 5'-GAATTC-3' (SEQ ID NO:2).

While not wishing to be bound by theory, it is thought that in nature, restriction endonucleases play a protective role in the welfare of the bacterial cell. They enable bacteria to resist infection by foreign DNA molecules like viruses and plasmids that would otherwise destroy or parasitize them. They impart resistance by binding to infecting DNA molecules and cleaving them in each place that the recognition sequence occurs. The disintegration that results inactivates many of the infecting genes and renders the DNA susceptible to further degradation by exonucleases.

A second component of restriction systems are the modification methylases. These enzymes are complementary to restriction endonucleases and they provide the means by which bacteria are able to protect their own DNA and distinguish it from foreign, infecting DNA. Modification methylases recognize and bind to the same nucleotide recognition sequence as the corresponding restriction endonuclease, but instead of breaking the DNA, they chemically modify one or other of the nucleotides within the sequence by the addition of a methyl group. Following methylation, the recognition sequence is no longer bound or cleaved by the restriction endonuclease. The DNA of a bacterial cell is always modified, by virtue of the activity of its modification methylase and it is therefore insensitive to the presence of the endogenous restriction endonuclease. It is only unmodified, and therefore identifiably foreign, DNA that is sensitive to restriction endonuclease recognition and attack. More than 3000 restriction endonucleases have been isolated from various bacterial strains. Of these, more than 200 recognize unique sequences, while the rest share common recognition specificities. Restriction endonucleases which recognize the same nucleotide sequence are termed "isoschizomers." Although the recognition sequences of isoschizomers are the same, they may vary with respect to site of cleavage (e.g., XmaI v. SmaI, Endow, et al., *J. Mol. Biol.* 112:521 (1977); Waalwijk, et al., *Nucleic Acids Res.* 5:3231 (1978)) and in cleavage rate at various sites (XhoI v. PaeR7I, Gingeras, et al., *Proc. Natl. Acad. Sci. U.S.A.* 80:402 (1983)).

There is a continuing need for novel type II restriction endonucleases. Although type II restriction endonucleases which recognize a number of specific nucleotide sequences are currently available, new restriction endonucleases which recognize novel sequences provide greater opportunities and ability for genetic manipulation. Each new unique endonuclease enables scientists to precisely cleave DNA at new positions within the DNA molecule, with all the opportunities this offers.

SUMMARY OF THE INVENTION

In accordance with the present invention, there is provided a novel restriction endonuclease obtainable from *Helicobacter pylori* CH4 (NEB#1236), hereinafter referred to as "HpyCH4IV", which endonuclease:

(1) recognizes the nucleotide sequence 5'-ACGT-3' in a double-stranded DNA molecule as shown below,
  5'-A↓CGT-3'
  3'-TGC↑A-5'
  (wherein G represents guanine, C represents cytosine, A represents adenine, T represents thymine and N represents either G, C, A, or T);

(2) cleaves said sequence in the phosphodiester bonds between the A and C as indicated with the arrows; and (3) cleaves double-stranded PhiX174 DNA to produce 19 fragments, including fragments of 1036, 749, 397, 379, 371, 365, 362, 343, 282, 282, 268 base pairs, and 8 fragments smaller than 200 base pairs.

The present invention further relates to a process for the production of the novel restriction endonuclease HpyCH4IV. This process comprises either culturing *Helicobacter pylori* CH4 under conditions suitable for expressing HpyCH4IV, collecting the cultured cells, obtaining a cell-free extract therefrom and separating and collecting the restriction endonuclease HpyCH4IV from the cell-free extract, or culturing a transformed host, such as *E. coli*, containing the genes for the HpyCH4IV methylase and endonuclease, collecting the cultured cells, obtaining a cell-free extract therefrom and separating and collecting the restriction endonuclease HpyCH4IV from the cell-free extract.

BRIEF DESCRIPTION OF THE FIGURES

FIG. 3—Map and DNA sequence of a portion of the HpyCH4IV gene locus FIG. 3A (SEQ ID NO:3, SEQ ID NO:4, FIG. 3B SEQ ID NO:5, SEQ ID NO:6, FIG. 3C SEQ ID NO:7, and SEQ ID NO:8).

DETAILED DESCRIPTION OF THE INVENTION

Figure 1:
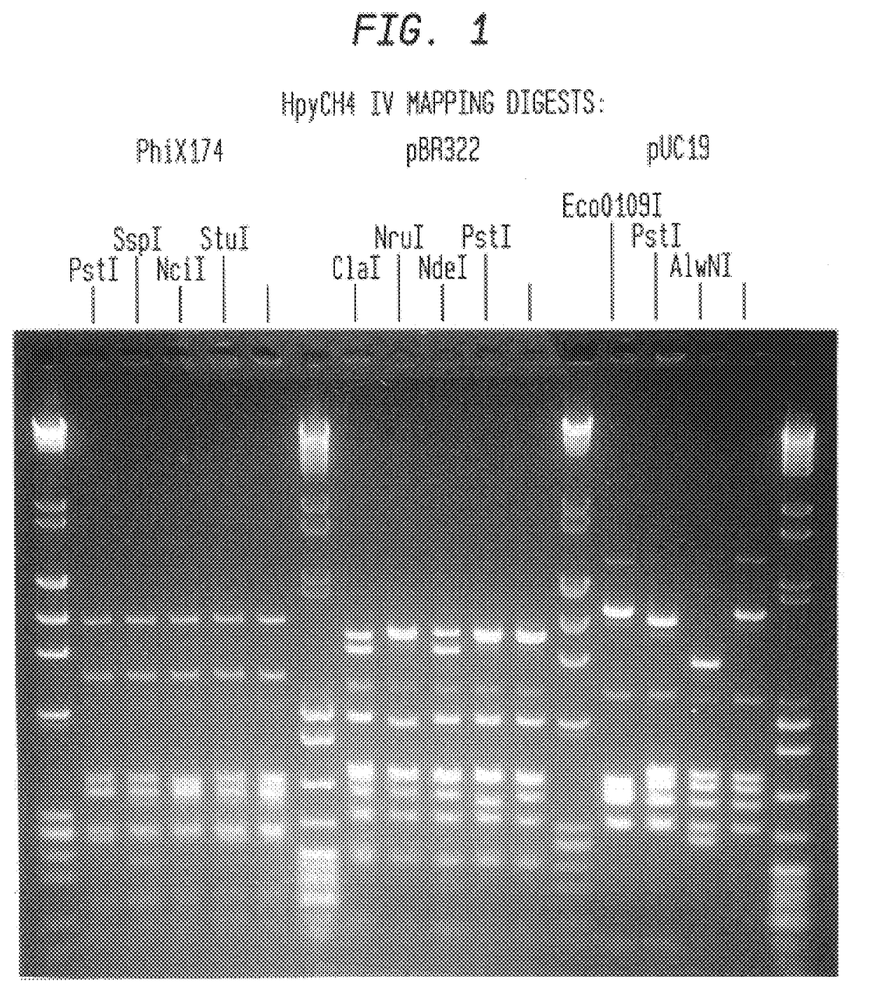
FIG. 1—Agarose gel showing HpyCH4IV cleavage of various DNAs.

The recognition sequence of the endonuclease of the present invention may be determined by mapping the locations of several HpyCH4IV cleavage sites in various DNAs and comparing the DNA sequences of these regions for homology, then comparing the predicted cleavage fragments of the putative recognition sequence with the observed restriction fragments produced by HpyCH4IV cleavage of various DNAs. The endonuclease HpyCH4IV was found to cleave PhiX174 DNA more than ten times, producing fragments of approximately 1025, 750, 400, 370, 350 and 280 bp, along with a number of smaller fragments. The location of several cut sites were mapped to approximate positions of 5300 and 265 (the 350 bp fragment) and 870 and 1225 (the 370 bp fragment) by simultaneously digesting PhiX174 DNA with HpyCH4IV and with endonucleases which cleave at known positions, such as SspI, NciI, StuI and PstI (FIG. 1). The approximate size of several of the larger DNA fragments produced by HpyCH4IV digestion of PhiX174 DNA were entered into the program SITES (Gingeras, et al., *Nucl. Acids Res.* 5:4105 (1978)), which generates potential recognition sequences for the input data by comparing the fragment sizes which would result from cleavage of the DNA at any given recognition pattern with the input fragment sizes. One such potential pattern generated was 5'-ACGT-3', which occurs in PhiX174 DNA at positions consistent with the mapping data obtained, i.e. at positions 5302 and 259 (a 343 bp fragment), and 865 and 1227 (a 362 bp fragment), as well as 15 other sites. The size of fragments predicted for cleavage at 5'-ACGT-3' sites in PhiX174, pBR322, pUC19, T7 and lambda DNAs matched the observed size of fragments from cleavage of these DNAs with HpyCH4IV, from which we conclude that HpyCH4IV recognizes the sequence 5'-ACGT-3'.

Figure 2:
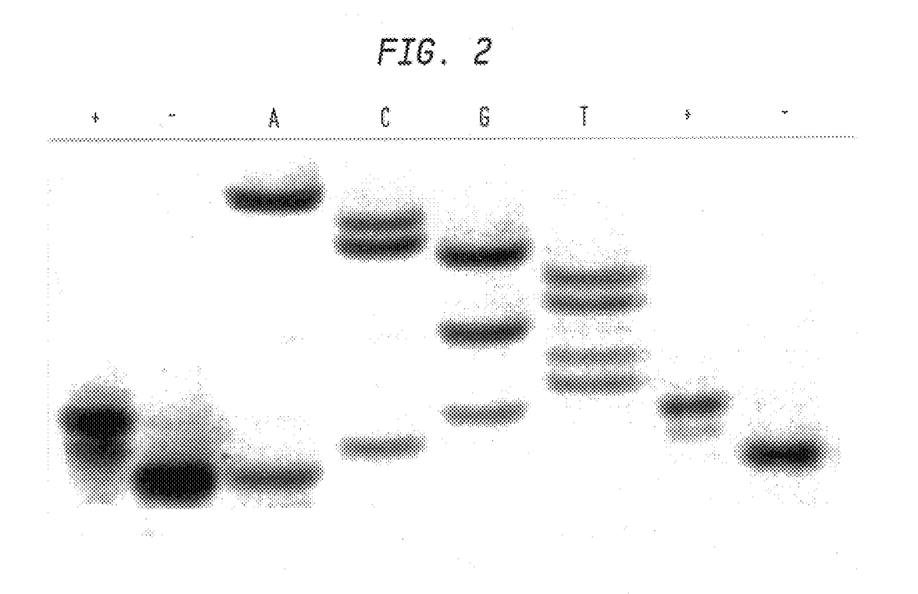
FIG. 2—Determination of the HpyCH4IV cleavage site.

The point of cleavage within the HpyCH4IV recognition sequence may be determined through dideoxy sequencing analysis of the terminal base sequence obtained from HpyCH4IV cleavage of a suitable DNA substrate (Sanger, et al., *PNAS* 74:5463–5467 (1977) Brown, et al., *J. Mol. Biol.* 140:143–148 (1980)). By the above referenced method (FIG. 2, exemplified in Example II) is was found that HpyCH4IV cleaves the phosphodiester bond between the A and the C in the recognition sequence 5'-A↓CGT-3' to produce a 2 base 5' extension, as indicated by the arrows:

5'-A↓CGT-3'

3'-TGC↑A-5'

In accordance with the present invention, HpyCH4IV is obtained by culturing *Helicobacter pylori* CH4 and recovering the endonuclease from the cells. A sample of *Helicobacter pylori* CH4 (NEB#1236) has been deposited under the terms and conditions of the Budapest Treaty with the American Type Culture Collection (ATCC) on Sep. 23, 1999 and bears the Patent Accession No. PTA-781.

For recovering the enzyme of the present invention *Helicobacter pylori* CH4 (NEB#1236) may be grown using any suitable technique. For example, *Helicobacter pylori* CH4 may be grown in Brucella broth media (BBL Microbiology Systems, Cockeysville, Md.) incubated anaerobically under 5% $CO_2$ at 37° C. Cells in the late logarithmic stage of growth are collected by centrifugation and either disrupted immediately or stored frozen at −70° C.

The HpyCH4IV enzyme can be isolated from *Helicobacter pylori* CH4 cells by conventional protein purification techniques. For example, cell paste is suspended in a buffer solution and treated by sonication, high pressure dispersion or enzymatic digestion to allow extraction of the endonuclease by the buffer solution. Intact cells and cellular debris are then removed by centrifugation to produce a cell-free extract containing HpyCH4IV. The HpyCH4IV endonuclease is then purified from the cell-free extract by ion-exchange chromatography, affinity chromatography, molecular sieve chromatography, or a combination of these methods to produce the endonuclease of the present invention.

The endonuclease of the present invention along with its corresponding methylase may also be obtained using recombinant DNA techniques, such as the methylation selection technique disclosed by Wilson, et al., U.S. Pat. No. 5,200,333. As an example, DNA from a bacterial strain which contains an R-M system (restruction-modification), such as *Helicobacter pylori*, is purified, partially digested with suitable Type II endonucleases, and ligated to an appropriate cleaved, dephosphorylated cloning vector. The ligated DNA is transformed into an appropriate host, such as *E. coli*, the transformants are pooled and the population of cloning vectors are purified to form libraries. The library of clones is then challenged by digesting with an endonuclease which will selectively destroy vectors which do not contain and express the methylase of the R-M system (restruction-modification) being cloned. Vectors which contain and express the methylase gene of interest will be modified at the endonuclease recognition sites of the challenging endonuclease and thus be immune from cleavage. The challenged clone pools are then transformed back into the appropriate host to recover the undigested, presumably methylase expressing clones. The transformants may be screened for endonuclease activity or cycled through further rounds of purification and selection. Finally, individual transformants are selected and their DNA purified. These clones are analyzed for resistance to cleavage by the endonuclease of interest and for common insert DNA. Cell extracts prepared from transformants which demonstrate endonuclease resistance are assayed in vitro for methyltransferase and endonuclease activities.

The present invention is further illustrated by the following Examples. These Examples are provided to aid in the understanding of the invention and are not construed as a limitation thereof.

The references cited above and below are herein incorporated by reference.

EXAMPLE I

PRODUCTION OF HpyCH4IV ENDONUCLEASE

*Helicobacter pylori* CH4 strain NEB#1236 was grown in Brucella broth media. The cells were incubated anaerobically under 5% $CO_2$ at 37° C. until late logarithmic stage. The cells were then harvested by centrifugation and stored frozen at −70° C.

8 grams of the cells obtained above were suspended in 40 mls buffer A (20 mM Tris-HCl, 0.1 mM EDTA, 1 mM dithiothreitol, 5% glycerol, pH 7.6 at 25° C.) adjusted to 50 mM NaCl. The cell suspension was sonicated until approximately 50 mg protein per gram of cells was released. The lysate was centrifuged at 15,000 rpm for 20 minutes at 4° C. in a Beckman JA17 rotor. 44 ml of supernatant was obtained containing approximately 400 mg of soluble protein.

The supernatant solution was applied to a 20 ml Heparin Hyper-D column (Biosepra, Marlborough, Mass.) equilibrated in buffer A adjusted to 50 mM NaCl. A 40 ml wash of buffer A adjusted to 50 mM NaCl was applied, then a 200 ml linear gradient of NaCl from 50 mM to 1M in buffer A was applied and fractions of 4 ml were collected. Fractions were assayed for HpyCH4IV endonuclease activity by incubation with 1 µg Lambda DNA (NEB) in 50 µl NEBuffer 4 for one hour at 37° C. HpyCH4IV activity eluted at 0.3M to 0.38M NaCl.

The Heparin Hyper-D column fractions containing the HpyCH4IV activity were pooled, diluted to 100 mM NaCl in buffer A and applied to a 3 ml Heparin-TSK column (Toso-Haas, Philadelphia, Pa.), and a 50 ml linear gradient from 0.1M to 0.6M NaCl in buffer A was applied to the Heparin-TSK column. The HpyCH4IV activity eluted between O.1M to 0.15M NaCl. The Heparin-TSK fractions containing HpyCH4IV activity were pooled, diluted to 50 mM NaCl in buffer A and applied to a 1 ml Mono-Q column (Pharmacia, Piscataway, N.J.), and a 50 ml linear gradient from 0.1 M to 0.6 M NaCl in buffer A was applied to the column. The HpyCH4IV activity was found in the flow-through. This pool was applied to a 1 mL Heparin HiTrap column (Pharmacia) and the protein solution was eluted with a 50 ml linear gradient of 50 mM to 1M MaCl in buffer A and fractions were tested for HpyCH4IV activity. The HpyCH4IV activity eluted between 0.5 M to 0.54 M NaCl and contained approximately 300 units of endonuclease activity. The HpyCH4IV obtained was substantially pure and free of contaminating endonuclease and exonuclease activities. Bovine serum albumin was added as a stabilizer to a final concentration of 200 µg/ml and the HpyCH4IV enzyme was dialyzed against storage buffer (50% glycerol, 50 mM NaCl, 20 mM Tris-HCl, 0.1 mM dithiothreitol, pH 7.5).

Activity Determination

HpyCH4IV activity: Samples of from 1 to 10 µls were added to 50 µls of substrate solution consisting of 1X NEBuffer 4 containing 1 µg Lambda phage DNA. The reaction was incubated at 37° C. for 5 to 60 mins. The reaction was terminated by adding 15 µls of a stop solution (50% glycerol, 50 mM EDTA pH 8.0, and 0.02% Bromophenol Blue). The reaction mixture was applied to a 1.2% agarose gel and electrophoresed. The bands obtained were identified in comparison with DNA size standards.

Unit Definition: One unit of HpyCH4IV is defined as the amount of HpyCH4IV required to completely cleave 1.0 µg of Lambda DNA in a total reaction volume of 50 µl NEBuffer 4, supplemented with 100 µg/ml bovine serum albumin, within one hour at 37° C.

EXAMPLE II

DETERMINATION OF THE HpyCH4IV CLEAVAGE SITE

The location of HpyCH4IV cleavage relative to the recognition sequence was determined by cleavage of a primer extension product, which was then electrophoresed alongside a set of standard dideoxy sequencing reactions produced from the same primer and template. pNEB193 DNA was employed as the template utilizing an HpyCH4IV recognition site at position 1952, conveniently located 22 bp 3' of a priming site for the primer NEB#1206 (5'-dGCTAGAGTAAGTAGTT-3' (SEQ ID NO:9).

Sequencing Reactions

The sequencing reactions were performed using the Sequenase version 2.0 DNA sequencing kit (Amersham Life Science) with modifications for the cleavage site determination. The template and primer were assembled in a 0.5 mL eppendorf tube by combining 2.5 µl dH20, 3 µl 5X sequencing buffer (200 mM Tris pH 7.5, 250 mM NaCl, 100 mM MgCl2), 8 µl pNEB193 double-stranded, denatured DNA (4 µg) and 1.5 µl of primer (NEB#1206 at 3.2 µM concentration). The double-stranded template was denatured by heating to 95° C. for 5 minutes, then added directly to the reaction. The primer-template solutions were incubated at 65° C. for 2 minutes, then cooled to 37° C. over 20 minutes in a beaker of 65° C. water on the benchtop to anneal the primer. The labeling mix (diluted 1:20) and sequenase were diluted according to manufacturer's instructions. The annealed primer and template tube was placed on ice. To this tube were added 1.5 µl 100 mM DTT, 3 pl diluted dGTP labeling mix, 1 µl [α-$^{33}$p] dATP (2000 Ci/mmole, 10 mCi/ml) and 3 µl diluted T7 Sequenase polymerase. The reaction was mixed and incubated at room temperature for 4 minutes. 3.5 µl of this reaction was then transferred into each of four tubes containing 2.5 µl termination mix for the A, C, G and T sequencing termination reactions. To the remaining reaction was added to 10 µl of Sequence Extending Mix, which is a mixture of dNTPs (no ddNTPs) to allow extension of the primer through and well beyond the HpyCH4IV site with no terminations to create a labeled strand of DNA extending through the HpyCH4IV recognition site for subsequent cleavage. The reactions were incubated 5 minutes at 37° C. To the A, C, G and T reactions were added 4 µl of stop solution and the samples were stored on ice. The extension reaction was then incubated at 70° C. for 20 minutes to inactivate the DNA polymerase (Sequenase), then cooled on ice. 10 µl of the extension reaction was then placed in one 0.5 ml eppendorf tube while 7 µl was placed in a second tube. To the first tube was added 1 µl (approximately 1 unit) HpyCH4IV endonuclease, the reaction was mixed, and then 2 µl was transferred to the second tube. These enzyme digest reactions were mixed and then incubated at 37° C. for 1 hour, following which the reactions were divided in half. To one half 4 µl of stop solution was added and mixed (the minus polymerase reaction). To the second half was added 0.4 ul Klenow DNA polymerase (NEB#210) containing 80 uM dNTPs and the reactions were incubated at room temperature for 15 minutes, following which 4 µl of stop solution was added. The sequencing reaction products were electrophoresed on an 6% Bis-Acrylamide sequencing gel (Novex QuickPoint system), with the HpyCH4IV digestions of the extension reaction next to the set of sequencing reactions produced from the same primer and template combination.

Results:

Digestion of the extension reaction product from primer NEB#1206 with HpyCH4IV endonuclease produced a band which co-migrated with the A nucleotide of the HpyCH4IV recognition sequence 5'-ACGT-3', indicating cleavage between the A and the C of the recognition sequence. Treatment of the cleaved extension reaction product with Klenow DNA polymerase produced a band which co-migrated with the G nucleotide of the HpyCH4IV recognition sequence 5'-ACGT-3', indicating cleavage between the A and the C of the recognition sequence on the opposite strand of DNA as well (FIG. 2). These results indicate HpyCH4IV cleaves DNA between the A and C in its recognition sequence on both DNA strands, 5'-A↓CGT-3', to produce a two base 5' extension.

EXAMPLE III

CLONING THE HpyCH4IV METHYLASE

1. DNA purification: To prepare the genomic DNA of *Helicobacter pylori* CH4, 1 gram of cell paste was resuspended in 10 ml of 25% sucrose, 0.05 M Tris-HCl pH 8.0, to which was added 5 ml of 0.25 M EDTA, pH 8.0. Then 3 ml of lysozyme solution (10 mg/ml lysozyme in 0.25 M Tris-HCl, pH 8.0) was added and the cell suspension was incubated at 4° C. for 16 hours. 12 ml of Lytic mix (1% Triton-X100, 0.05 M Tris, 62 mM EDTA, pH 8.0) and 2.5 ml of 10% SDS was then added and the solution was incubated at 37° C. for 5 minutes. The solution was extracted with one volume of equilibrated phenol:chloroform:isoamyl alcohol (50:48:2, v/v/v) and the aqueous phase was recovered and extracted with one volume of chloroform:isoamyl alcohol (24:1, v/v) two times. The aqueous solution was then dialysed against four changes of 2 L of 10 mM Tris, 1 mM EDTA, pH 8.0. The dialysed DNA solution was digested with RNase (100 $\mu$g/ml) at 37° C. for 1 hour. The DNA was precipitated by the addition of $\frac{1}{10}$th volume 5 M NaCl and 0.55 volumes of 2-propanol and spooled on a glass rod. The DNA was briefly rinsed in 70% ethanol, air dried and dissolved in 3 ml TE (10 mM Tris, 1 mM EDTA, pH 8.0) to a concentration of approximately 300 mg/ml and stored at 4° C.

2. Construction of libraries of genomic *Helicobacter pylori* CH4 DNA in a selectable vector: *Helicobacter pylori* CH4 genomic DNA was partially digested with frequent cutting enzymes, Sau3AI or AciI. The partial digestion was carried out by serial dilution of the Sau3AI or AciI restriction endonuclease from 0.5 units/$\mu$g DNA to 0.016 units/$\mu$g in the manufacturer's reaction buffer and digesting at 37° C. for 1 hour. The reactions were subsequently terminated by phenol:chloroform extraction. Reactions which produced an average size range of fragments from 2 to 6 kb were used for library construction. 3 $\mu$g of this partially digested *H. pylori* CH4 genomic DNA was ligated to 1 $\mu$g of the vector pUC19 (previously cleaved by BamHI (Sau3AI) or AccI (AciI) and dephosphorylated with calf intestinal alkaline phosphatase) in a final volume of 50 $\mu$l in 1X NEB ligase buffer with 1000 units (NEB) of T4 DNA ligase. The ligation reactions were incubated at 16° C. for 16 hours. 10 ul of each ligation reaction mixture was then transformed by electroporation into *E. coli* ER2683 cells and grown out in 10 ml L-Broth for 1 hour. 10 $\mu$l was then plated onto L-Broth agar plates supplemented with 100 $\mu$g/ml ampicillin to count the number transformants and the plates were incubated at 37° C. overnight. The remaining outgrowth was grown overnight in 250 ml L-Broth supplemented with 100 $\mu$g/ml ampicillin with shaking at 37° C. A total of $5 \times 10^4$ individual transformants were obtained for the Sau3Ai library, and $1 \times 10^5$ transformants for the AciI library. The cells of the 250ml liquid culture were harvested by centrifugation at 5 K rpm for 5 minutes. The plasmids from these cells were purified by a standard cesium chloride ultracentrifugation procedure, precipitated and resuspended in TE buffer at a concentration of 250 $\mu$g/ml.

3. HpyCH4IV methylase selection: 1 $\mu$g of each plasmid library was digested for 2 hours at 37° C. in 50 $\mu$l 1X NEB#4 buffer with 4 units of the HpyCH4IV prepared as above from *H. pylori* CH4 cells. 10 $\mu$l of this HpyCH4IV digestion reaction was then transformed into 100 $\mu$l *E. coli* ER2688 competent cells and plated on L-broth plates containing 100 $\mu$g/ml ampicillin and the plates incubated at 37° C. overnight. A total of 1600 transformants were obtained from the AciI library digested with 4 units of HpyCH4IV. These 1600 survivors were scraped off the plate and inoculated into 100 mL L-broth containing 100 $\mu$g/ml ampicillin and grown overnight with shaking. The cells were then harvested by centrifugation and plasmids were prepared from two 3 mL portions of the cells by Qiagen QIAprep® Spin Miniprep columns according to the manufacturers instructions. 1 $\mu$g of this plasmid pool was digested for 2 hours at 37° C. in 50 $\mu$l 1X NEB#4 buffer with 4 units of HpyCH4IV. 10 $\mu$l of this HpyCH4IV digestion reaction was then transformed into 100 $\mu$l *E. coli* ER2688 competent cells and plated on L-broth plates containing 100 $\mu$g/ml ampicillin and the plates incubated at 37° C. overnight. A total of 6 transformants were obtained and analyzed as follows: plasmid from each colony was isolated by miniprep procedures and digested with HpyCH4IV endonuclease.

Analysis of plasmid clones: Individual transformants were inoculated into 10 ml cultures of L-broth containing 100 $\mu$g/ml ampicillin and the plasmids that they carried were prepared by Qiagen QIAprep® Spin Miniprep columns according to the manufacturers instructions. Plasmids were assayed for the presence of the HpyCH4IV methylase by digestion with HpyCH4IV endonuclease.

All six clones analyzed from the AciI library were found to be fully protected from HpyCH4IV digestion. Further restriction analysis showed these clones all contained an insert of approximately 1800 bp in size, and all six clones produced the same size ApoI and HindIII restriction fragments. All six clones were tested for and found not to express HpyCH4IV restriction activity when grown in L-Broth containing 100 $\mu$g/ml ampicillin. DNA sequence from the ends of the clones was obtained as detailed below in Example IV.

EXAMPLE IV

SEQUENCING THE HpyCH4IV METHYLASE CLONES

Figure 3A:
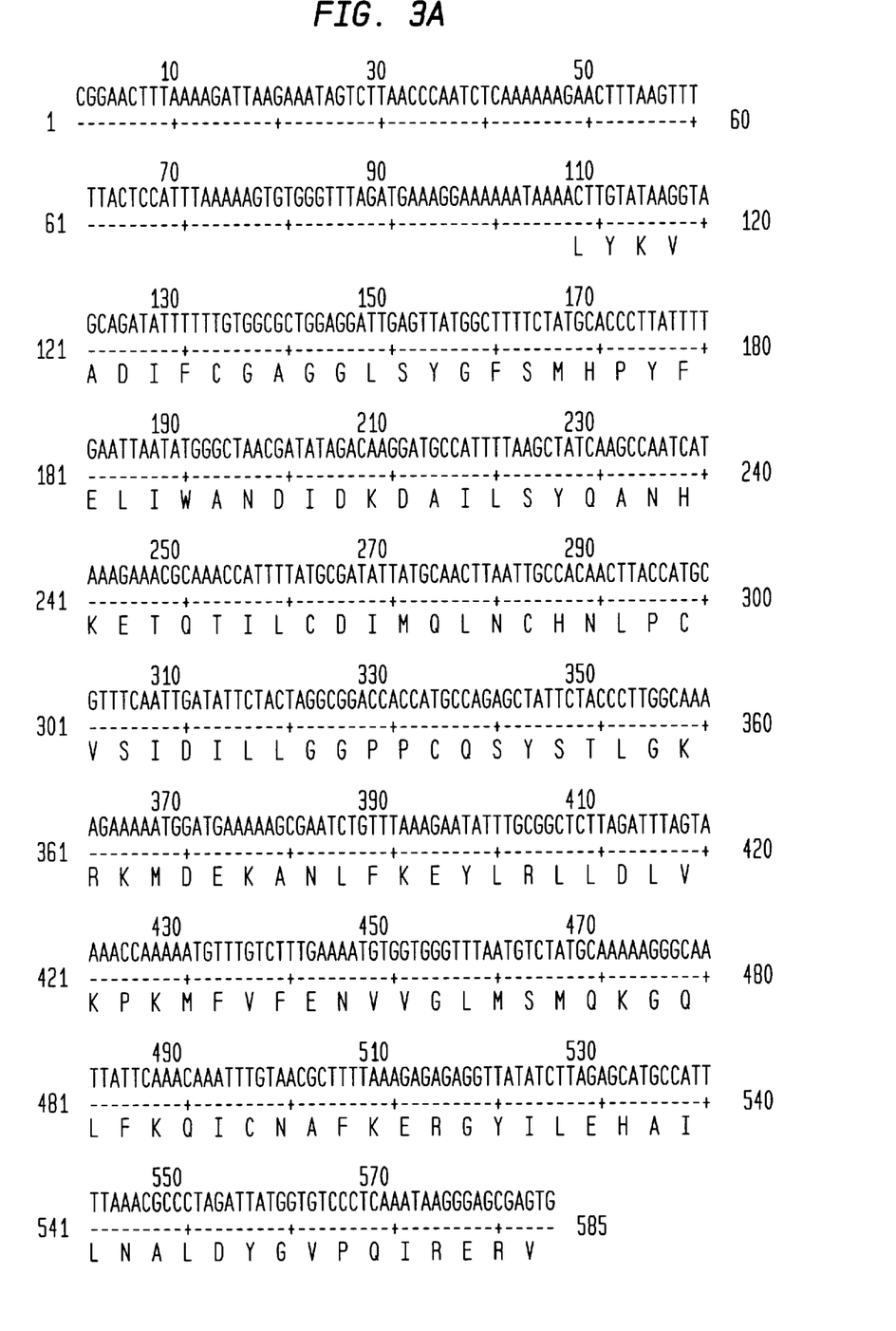
Figure 3B:
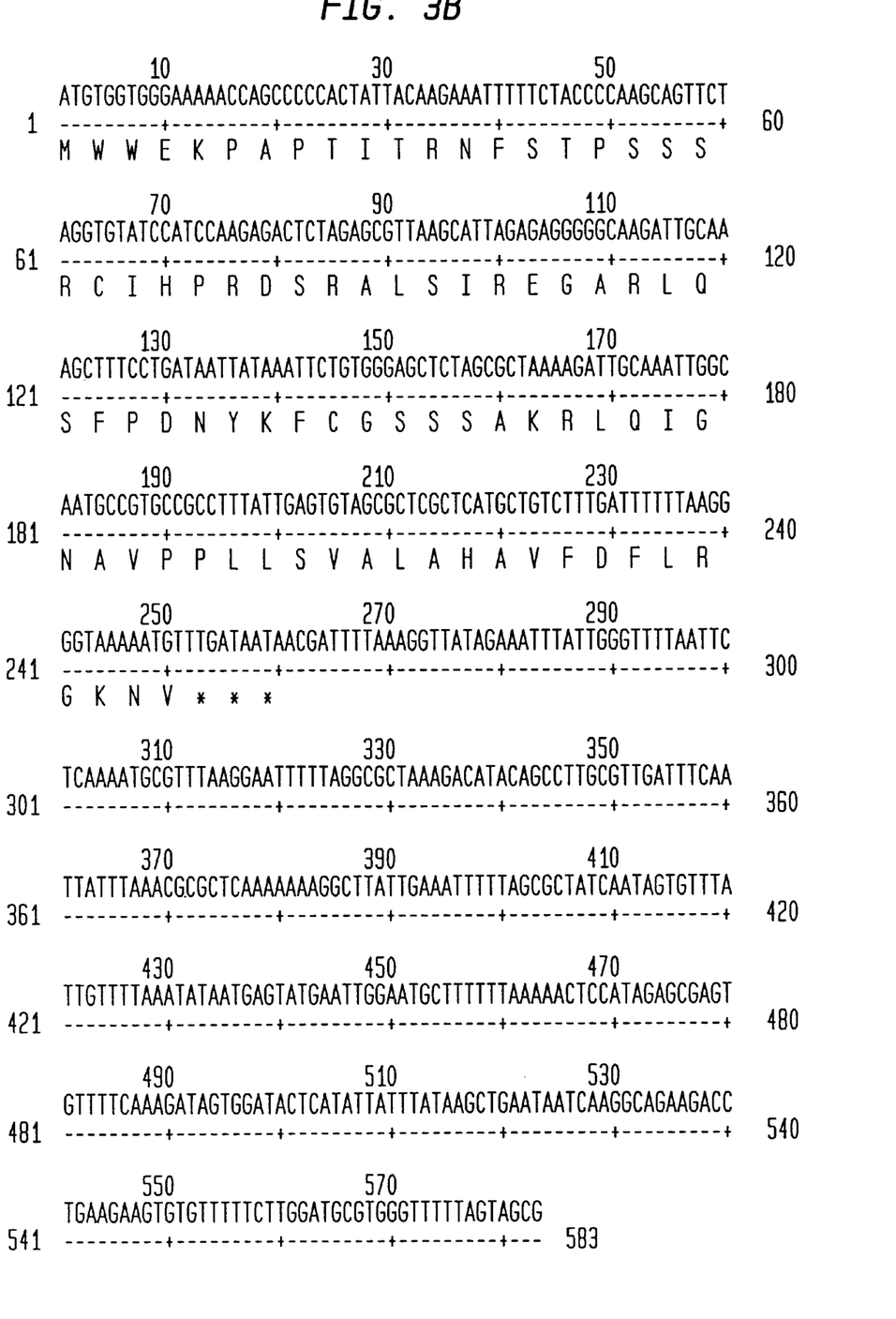
Figure 3C:
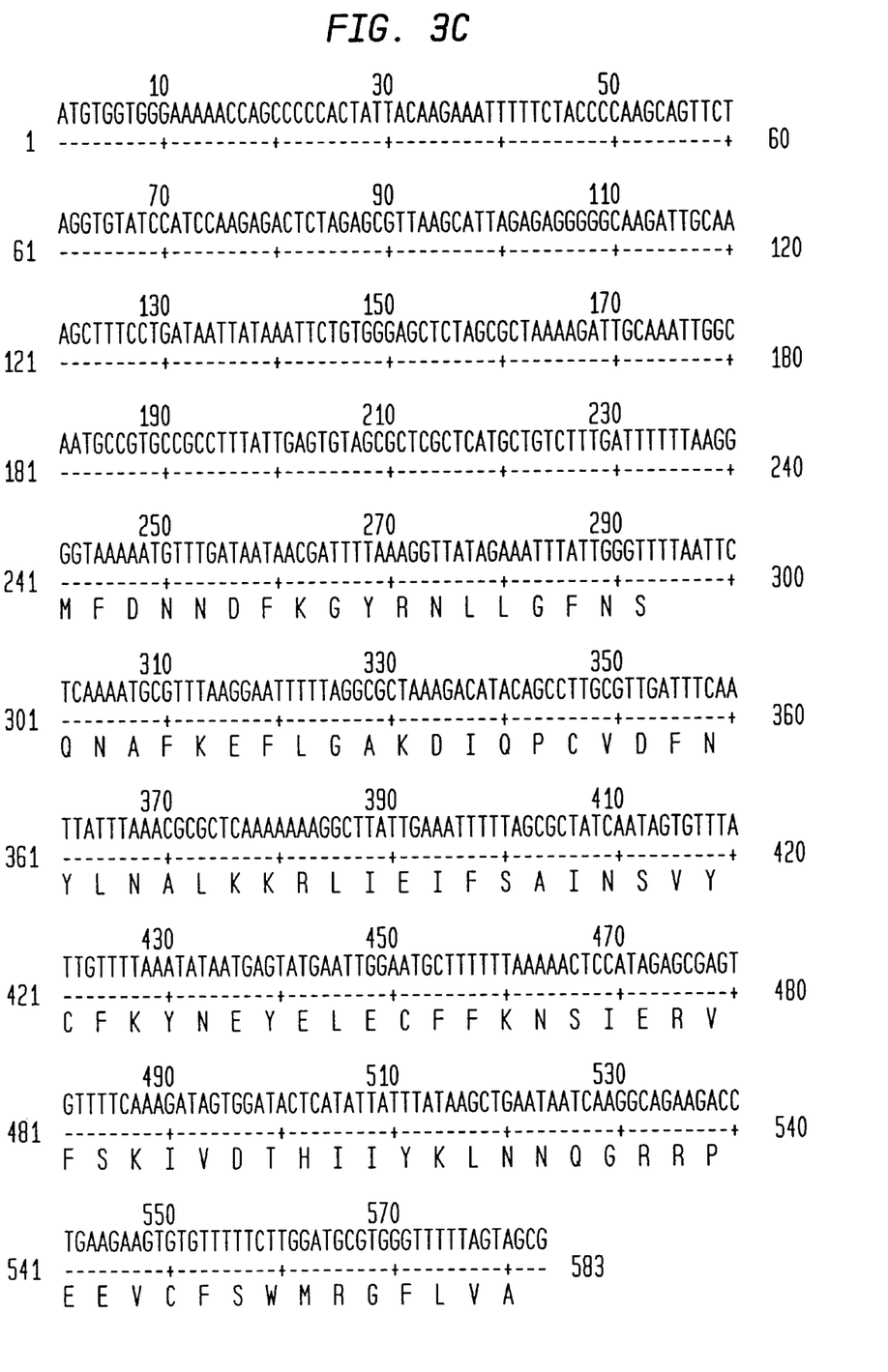

1. DNA Sequencing: DNA sequencing was performed on double-stranded templates on an ABI 373 automated sequencer. Individual clones were sequenced from primers located in the vector on both sides of the inserts. The DNA sequencing of the clones was incomplete at time of filing. Computer analyses of the DNA sequences obtained were performed with the Genetics Computer Group programs (Deverenx, et al., *Nucleic Acids Res.* 12:387–395 (1984)) and database similarity searches were performed via the internet at the National Center for Biotechnology Information site using the BLASTX algorithm (Altschul, et al., *J. Mol. Biol* 215:403–410 (1990) and Gish, et al., *Nature Genet.* 3:266–722 (1993).). An open reading frame (ORF) of 480 bp which contained motifs 1 through 8 characteristic of 5-methyl cytosine DNA methyltransferases was identified in DNA sequence reading into the cloned DNA from one end of the insert (SEQ ID NO:3 and SEQ ID NO:4, FIG. 3A). This partial open reading frame was identified as the N-terminal portion of the HpyCH4IV methyltransferase, designated HpyCH4IVM. DNA sequence from the other end of the *H. pylori* DNA insert revealed two partial open reading frames, the internal one of which contained typical 5-methyl cytosine methyltransferase motifs 9 and 10 (SEQ ID NO:5 and SEQ ID NO:6, FIG. 3B), indicating this is the C-terminal portion of the HpyCH4IV methyltransferase gene. The second ORF of 336 bp extends through the end of the cloned DNA fragment and an unknown length beyond. This ORF is believed to be the N-terminal portion of the HpyCH4IV endonuclease gene.

What is claimed is:

1. A substantially pure Type II restriction endonuclease obtainable from *Helicobacter pylori* (ATCC Accession No. PTA-781) recognizing the following base sequence in double-stranded deoxyribonucleic acid molecules:

5'-A↓CGT-3'
3'-TGC↑A-5' and having a cleavage position defined by the arrows.

2. The Type II restriction endonuclease of claim 1, wherein the restriction endonuclease is purified from *Helicobacter pylori* (ATCC Accession No. PTA-781).

3. A method for obtaining the Type II restriction endonuclease of claim 1, comprising cultivating a sample of *Helicobacter pylori* under conditions favoring the production of said endonuclease and separating said endonuclease therefrom.

* * * * *

UNITED STATES PATENT AND TRADEMARK OFFICE
CERTIFICATE OF CORRECTION

PATENT NO. : 6,194,188 B1
DATED : February 27, 2001
INVENTOR(S) : Richard D. Morgan and Qing Xu It is certified that error appears in the above-identified patent and that said Letters Patent is hereby corrected as shown below:

ABSTRACT,
Line 16, delete "282," second occurence

Column 2,
Line 57, delete "282," second occurence

Column 6,
Line 15, replace "MgCl2" with -- $MgCl_2$ --
Line 32, after "added" delete "to"
Line 55, replace "an" with -- a --

Column 8,
Line 57, replace "(1993).)." with -- (1993)). --

Signed and Sealed this

First Day of January, 2002

Attest:

JAMES E. ROGAN
*Attesting Officer*   *Director of the United States Patent and Trademark Office*

UNITED STATES PATENT AND TRADEMARK OFFICE
CERTIFICATE OF CORRECTION

PATENT NO. : 6,194,188 B1
DATED : February 27, 2001
INVENTOR(S) : Morgan et al.

It is certified that error appears in the above-identified patent and that said Letters Patent is hereby corrected as shown below:

Column 1,
Line 6, insert -- This invention was made with Government support under contract number DK53707 awarded by the National Institutes of Health. The Government has certain rights in the invention. --

Signed and Sealed this

Twenty-eighth Day of January, 2003

JAMES E. ROGAN
*Director of the United States Patent and Trademark Office*

```
                              SEQUENCE LISTING

<160> NUMBER OF SEQ ID NOS: 9

<210> SEQ ID NO 1
<211> LENGTH: 6
<212> TYPE: DNA
<213> ORGANISM: Haemophilus aegyptius

<400> SEQUENCE: 1 wggccw                                                                   6

<210> SEQ ID NO 2
<211> LENGTH: 6
<212> TYPE: DNA
<213> ORGANISM: Escherichia coli

<400> SEQUENCE: 2 gaattc                                                                   6

<210> SEQ ID NO 3
<211> LENGTH: 585
<212> TYPE: DNA
<213> ORGANISM: Helicobacter pylori
<220> FEATURE:
<221> NAME/KEY: CDS
<222> LOCATION: (109)..(585)

<400> SEQUENCE: 3
cggaacttta aagattaag aaatagtctt aacccaatct caaaaaagaa ctttaagttt          60
ttactccatt taaaaagtgt gggtttagat gaaaggaaaa aataaaac ttg tat aag        117
                                                    Leu Tyr Lys
                                                      1 gta gca gat att ttt tgt ggc gct gga gga ttg agt tat ggc ttt tct         165
Val Ala Asp Ile Phe Cys Gly Ala Gly Gly Leu Ser Tyr Gly Phe Ser
     5                  10                  15 atg cac cct tat ttt gaa tta ata tgg gct aac gat ata gac aag gat         213
Met His Pro Tyr Phe Glu Leu Ile Trp Ala Asn Asp Ile Asp Lys Asp
 20                  25                  30                  35 gcc att tta agc tat caa gcc aat cat aaa gaa acg caa acc att tta         261
Ala Ile Leu Ser Tyr Gln Ala Asn His Lys Glu Thr Gln Thr Ile Leu
                 40                  45                  50 tgc gat att atg caa ctt aat tgc cac aac tta cca tgc gtt tca att         309
Cys Asp Ile Met Gln Leu Asn Cys His Asn Leu Pro Cys Val Ser Ile
             55                  60                  65 gat att cta cta ggc gga cca cca tgc cag agc tat tct acc ctt ggc         357
Asp Ile Leu Leu Gly Gly Pro Pro Cys Gln Ser Tyr Ser Thr Leu Gly
         70                  75                  80 aaa aga aaa atg gat gaa aaa gcg aat ctg ttt aaa gaa tat ttg cgg         405
Lys Arg Lys Met Asp Glu Lys Ala Asn Leu Phe Lys Glu Tyr Leu Arg
     85                  90                  95 ctc tta gat tta gta aaa cca aaa atg ttt gtc ttt gaa aat gtg gtg         453
Leu Leu Asp Leu Val Lys Pro Lys Met Phe Val Phe Glu Asn Val Val
100                 105                 110                 115 ggt tta atg tct atg caa aaa ggg caa tta ttc aaa caa att tgt aac         501
Gly Leu Met Ser Met Gln Lys Gly Gln Leu Phe Lys Gln Ile Cys Asn
                120                 125                 130 gct ttt aaa gag aga ggt tat atc tta gag cat gcc att tta aac gcc         549
```

```
Ala Phe Lys Glu Arg Gly Tyr Ile Leu Glu His Ala Ile Leu Asn Ala
            135                 140                 145 cta gat tat ggt gtc cct caa ata agg gag cga gtg                            585
Leu Asp Tyr Gly Val Pro Gln Ile Arg Glu Arg Val
            150                 155

<210> SEQ ID NO 4
<211> LENGTH: 159
<212> TYPE: PRT
<213> ORGANISM: Helicobacter pylori

<400> SEQUENCE: 4

Leu Tyr Lys Val Ala Asp Ile Phe Cys Gly Ala Gly Gly Leu Ser Tyr
 1               5                  10                  15

Gly Phe Ser Met His Pro Tyr Phe Glu Leu Ile Trp Ala Asn Asp Ile
                20                  25                  30

Asp Lys Asp Ala Ile Leu Ser Tyr Gln Ala Asn His Lys Glu Thr Gln
            35                  40                  45

Thr Ile Leu Cys Asp Ile Met Gln Leu Asn Cys His Asn Leu Pro Cys
        50                  55                  60

Val Ser Ile Asp Ile Leu Leu Gly Gly Pro Pro Cys Gln Ser Tyr Ser
 65                 70                  75                  80

Thr Leu Gly Lys Arg Lys Met Asp Glu Lys Ala Asn Leu Phe Lys Glu
                85                  90                  95

Tyr Leu Arg Leu Leu Asp Leu Val Lys Pro Lys Met Phe Val Phe Glu
                100                 105                 110

Asn Val Val Gly Leu Met Ser Met Gln Lys Gly Gln Leu Phe Lys Gln
            115                 120                 125

Ile Cys Asn Ala Phe Lys Glu Arg Gly Tyr Ile Leu Glu His Ala Ile
        130                 135                 140

Leu Asn Ala Leu Asp Tyr Gly Val Pro Gln Ile Arg Glu Arg Val
145                 150                 155

<210> SEQ ID NO 5
<211> LENGTH: 583
<212> TYPE: DNA
<213> ORGANISM: Helicobacter pylori
<220> FEATURE:
<221> NAME/KEY: CDS
<222> LOCATION: (1)..(252)

<400> SEQUENCE: 5 atg tgg tgg gaa aaa cca gcc ccc act att aca aga aat ttt tct acc           48
Met Trp Trp Glu Lys Pro Ala Pro Thr Ile Thr Arg Asn Phe Ser Thr
 1               5                  10                  15 cca agc agt tct agg tgt atc cat cca aga gac tct aga gcg tta agc           96
Pro Ser Ser Ser Arg Cys Ile His Pro Arg Asp Ser Arg Ala Leu Ser
                20                  25                  30 att aga gag ggg gca aga ttg caa agc ttt cct gat aat tat aaa ttc          144
Ile Arg Glu Gly Ala Arg Leu Gln Ser Phe Pro Asp Asn Tyr Lys Phe
            35                  40                  45 tgt ggg agc tct agc gct aaa aga ttg caa att ggc aat gcc gtg ccg          192
Cys Gly Ser Ser Ser Ala Lys Arg Leu Gln Ile Gly Asn Ala Val Pro
        50                  55                  60 cct tta ttg agt gta gcg ctc gct cat gct gtc ttt gat ttt tta agg          240
Pro Leu Leu Ser Val Ala Leu Ala His Ala Val Phe Asp Phe Leu Arg
 65                 70                  75                  80 ggt aaa aat gtt tgataataac gattttaaag gttatagaaa tttattgggt              292
Gly Lys Asn Val
```

-continued

```
tttaattctc aaaatgcgtt taaggaattt ttaggcgcta aagacataca gccttgcgtt      352
gatttcaatt atttaaacgc gctcaaaaaa aggcttattg aaatttttag cgctatcaat      412
agtgtttatt gttttaaata taatgagtat gaattggaat gcttttttaa aaactccata      472
gagcgagtgt tttcaaagat agtggatact catattattt ataagctgaa taatcaaggc      532
agaagacctg aagaagtgtg ttttcttgg atgcgtgggt ttttagtagc g                583
```

<210> SEQ ID NO 6
<211> LENGTH: 84
<212> TYPE: PRT
<213> ORGANISM: Helicobacter pylori

<400> SEQUENCE: 6

```
Met Trp Trp Glu Lys Pro Ala Pro Thr Ile Thr Arg Asn Phe Ser Thr
 1               5                  10                  15

Pro Ser Ser Ser Arg Cys Ile His Pro Arg Asp Ser Arg Ala Leu Ser
            20                  25                  30

Ile Arg Glu Gly Ala Arg Leu Gln Ser Phe Pro Asp Asn Tyr Lys Phe
        35                  40                  45

Cys Gly Ser Ser Ser Ala Lys Arg Leu Gln Ile Gly Asn Ala Val Pro
    50                  55                  60

Pro Leu Leu Ser Val Ala Leu Ala His Ala Val Phe Asp Phe Leu Arg
65                  70                  75                  80

Gly Lys Asn Val
```

<210> SEQ ID NO 7
<211> LENGTH: 583
<212> TYPE: DNA
<213> ORGANISM: Helicobacter pylori
<220> FEATURE:
<221> NAME/KEY: CDS
<222> LOCATION: (248)..(583)

<400> SEQUENCE: 7

```
atgtggtggg aaaaaccagc ccccactatt acaagaaatt tttctacccc aagcagttct      60
aggtgtatcc atccaagaga ctctagagcg ttaagcatta gagaggggc aagattgcaa      120 agctttcctg ataattataa attctgtggg agctctagcg ctaaaagatt gcaaattggc      180
aatgccgtgc cgccttttatt gagtgtagcg ctcgctcatg ctgtctttga ttttttaagg      240 ggtaaaa atg ttt gat aat aac gat ttt aaa ggt tat aga aat tta ttg        289
        Met Phe Asp Asn Asn Asp Phe Lys Gly Tyr Arg Asn Leu Leu
          1               5                  10 ggt ttt aat tct caa aat gcg ttt aag gaa ttt tta ggc gct aaa gac        337
Gly Phe Asn Ser Gln Asn Ala Phe Lys Glu Phe Leu Gly Ala Lys Asp
 15                  20                  25                  30 ata cag cct tgc gtt gat ttc aat tat tta aac gcg ctc aaa aaa agg        385
Ile Gln Pro Cys Val Asp Phe Asn Tyr Leu Asn Ala Leu Lys Lys Arg
             35                  40                  45 ctt att gaa att ttt agc gct atc aat agt gtt tat tgt ttt aaa tat        433
Leu Ile Glu Ile Phe Ser Ala Ile Asn Ser Val Tyr Cys Phe Lys Tyr
         50                  55                  60 aat gag tat gaa ttg gaa tgc ttt ttt aaa aac tcc ata gag cga gtg        481
Asn Glu Tyr Glu Leu Glu Cys Phe Phe Lys Asn Ser Ile Glu Arg Val
     65                  70                  75 ttt tca aag ata gtg gat act cat att att tat aag ctg aat aat caa        529
Phe Ser Lys Ile Val Asp Thr His Ile Ile Tyr Lys Leu Asn Asn Gln
 80                  85                  90
```

-continued

```
ggc aga aga cct gaa gaa gtg tgt ttt tct tgg atg cgt ggg ttt tta    577
Gly Arg Arg Pro Glu Glu Val Cys Phe Ser Trp Met Arg Gly Phe Leu
 95             100                 105                 110 gta gcg                                                            583
Val Ala

<210> SEQ ID NO 8
<211> LENGTH: 112
<212> TYPE: PRT
<213> ORGANISM: Helicobacter pylori

<400> SEQUENCE: 8

Met Phe Asp Asn Asn Asp Phe Lys Gly Tyr Arg Asn Leu Leu Gly Phe
 1               5                  10                  15

Asn Ser Gln Asn Ala Phe Lys Glu Phe Leu Gly Ala Lys Asp Ile Gln
            20                  25                  30

Pro Cys Val Asp Phe Asn Tyr Leu Asn Ala Leu Lys Lys Arg Leu Ile
        35                  40                  45

Glu Ile Phe Ser Ala Ile Asn Ser Val Tyr Cys Phe Lys Tyr Asn Glu
    50                  55                  60

Tyr Glu Leu Glu Cys Phe Phe Lys Asn Ser Ile Glu Arg Val Phe Ser
 65                 70                  75                  80

Lys Ile Val Asp Thr His Ile Ile Tyr Lys Leu Asn Asn Gln Gly Arg
                85                  90                  95

Arg Pro Glu Glu Val Cys Phe Ser Trp Met Arg Gly Phe Leu Val Ala
            100                 105                 110

<210> SEQ ID NO 9
<211> LENGTH: 16
<212> TYPE: DNA
<213> ORGANISM: Helicobacter pylori

<400> SEQUENCE: 9
gctagagtaa gtagtt                                                   16
```